United States Patent
Whittle (12)

(10) Patent No.: US 6,849,274 B1
(45) Date of Patent: Feb. 1, 2005

(54) NUTRITIONAL AND PHARMACEUTICAL COMPOSITIONS

(76) Inventor: Brian Anthony Whittle, "Mere Close" Hull Road, Hornsea, East Yorkshire, HU18 1RJ (GB)

( * ) Notice: Subject to any disclaimer, the term of this patent is extended or adjusted under 35 U.S.C. 154(b) by 0 days.

(21) Appl. No.: 09/787,806

(22) PCT Filed: Sep. 24, 1999

(86) PCT No.: PCT/GB99/03196

§ 371 (c)(1),
(2), (4) Date: May 8, 2001

(87) PCT Pub. No.: WO00/18259

PCT Pub. Date: Apr. 6, 2000

(30) Foreign Application Priority Data

Sep. 25, 1998 (GB) .............................. 9820815

(51) Int. Cl.[7] .................. A61K 33/08; A61K 33/06; A61K 33/04; A61K 9/46; A61K 9/14
(52) U.S. Cl. .................. 424/600; 424/682; 424/688; 424/703; 424/709; 424/400; 424/439; 424/464; 424/465; 424/466; 424/489
(58) Field of Search .................. 424/400, 439, 424/464, 465, 466, 489, 600, 682, 688, 703, 709

(56) References Cited

U.S. PATENT DOCUMENTS

| | | | | |
|---|---|---|---|---|
| 2,297,599 A | * | 9/1942 | Wilen | 424/466 |
| 4,036,228 A | * | 7/1977 | Theeuwes | 128/260 |
| 5,502,232 A | * | 3/1996 | Buysch et al. | 558/270 |
| 5,776,431 A | * | 7/1998 | Galat | 424/44 |
| 5,993,854 A | * | 11/1999 | Needleman et al. | 424/466 |
| 6,066,342 A | * | 5/2000 | Gurol et al. | 424/687 |

FOREIGN PATENT DOCUMENTS

WO    WO 96/22704 A1 *  8/1996 ............. A23L/2/44

* cited by examiner

*Primary Examiner*—Thurman K. Page
*Assistant Examiner*—Simon J. Oh
(74) *Attorney, Agent, or Firm*—Rader, Fishman & Grauer, PLLC

(57) ABSTRACT

Th present invention relates to nutritional and pharmaceutical compositions. More particularly it is concerned with improving compositions which due to the presence of an efflorescent component may be unstable and prone to decomposition and/or spoilage. The problem is overcome by incorporating one or mote anhydrous compounds into the composition in an amount capable of sequestering any water which may be released from one or more water containing components. The preferred anhydrous compounds are anhydrous or calcined $MgSO_4$ and CaO.

15 Claims, No Drawings

NUTRITIONAL AND PHARMACEUTICAL COMPOSITIONS

The present invention relates to nutritional and pharmaceutical compositions.

More particularly it is concerned with improving compositions which due to the presence of an efflorescent component may be unstable and prone to decomposition and/or spoilage.

The release of "bound" water in so called "dry compositions" can activate degenerative reactions for a variety of reasons. In such compositions water may be bound as water of crystallisation. Where the composition contains a salt that has water of crystallisation, variations in temperature can cause release of this bound water. If the composition is contained in a closed environment such as a hermetically sealed sachet, then the water vapour released may subsequently condense and produce a micro environment in which the amount of moisture is sufficient to cause a chemical reaction or microbial spoilage. In the closed environment of a sachet of an effervescent preparation, the, presence of moisture can lead to a premature reaction. This is manifested as evolution of gas which in extreme cases "blow" the sachet but more typically leads to a composition with a reduced activity.

Where pharmaceutical and nutritional compositions are known to be particularly sensitive to the presence of moisture, it is necessary to take precautions to reduce the effects of water vapour. It is thus necessary to carry out production in an environment with a low relative humidity. It is also conventional to include a packaged desiccant in the pack in which the product is enclosed. Typically, desiccants used in such packs contain silica gel enclosed in a cartridge or porous sachet. The capacity of these desiccant sachets is variable, depending for their efficacy on the conditions under which they have been stored previously.

The mobility of water that is "locked up" in a salt as water of crystallisaton is a problem affecting the stability of nutritional and pharmaceutical compositions.

It is an aim of the present invention to provide a nutritional or pharmaceutical composition which is less prone to decomposition and/or spoilage.

According to a first aspect of the present invention there is provided a nutritional or pharmaceutical composition comprising one or more water containing components in which the water is releasably bound wherein one or more anhydrous compounds are mixed in the composition in an amount capable of sequestering any water which may be released from the one or more water containing components to provide a continuous desiccant effect under normal handling conditions.

The one or more anhydrous compounds and/or their hydrated forms should themselves be nutritionally or pharmaceutically acceptable.

Preferably the one or more anhydrous compounds are selected from CaO and anhydrous or calcined $MgSO_4$.

Since calcium salts have a constipating action and magnesium salts have the opposite effect it is preferred to incorporate both calcium and magnesium salts to counter their individual effects.

More preferably still the calcium and magnesium present in the composition are present together, more preferably still in the form of CaO and anhydrous or calcined $MgSO_4$.

Preferably the calcium and magnesium in the product are present in amounts sufficient to provide a recommended daily allowance of calcium and magnesium.

Preferably the CaO is present in an amount of up to 10% of the composition (by weight) and more preferably still from 4–8%.

Preferably the magnesium is present as anhydrous or calcined $MgSO_4$.

Preferably the anhydrous or ca kind $MgSO_4$ is present in an amount of up to 10% of the composition (by weight) and more preferably still from 1–5%.

The problem of stability is particularly acute where the composition is intended to effervesce. Such compositions contain an acid, usually in the form of a salt and a carbonate or bicarbonate. The effervescence is caused by a reaction between the acid and carbonate or bicarbonate when the composition is dissolved in water. These compositions, which are often packaged in sachets, are particularly prone to decomposition as the acid salt used, frequently a fruit acid salt, is often calcium lactate, a pentahydrate. The water of crystallisation effloresces causing release of $CO_2$ and "blowing" of the sachets. By intimately mixing the composition with one or more nutritionally or pharmaceutically acceptable anhydrous compounds in amounts capable of sequestering any water which may be released from the one or more water containing components of the composition a continuous desiccant effect is provided and the problem is overcome.

Preferably the compositions will include a component, for example, a sulphide, which releases $SO_2$ in the presence of free water. This has an antimicrobial effect on the composition.

In one embodiment the one or more anhydrous compounds are provided in the form of a premix.

According to a further aspect of the present invention there is provided a composition premix comprising an acid or salt thereof in admixture with an anhydrous compound which has a greater avidity for water than the acid or salt thereof.

According to yet a further aspect of the present invention there is provided the use of CaO and/or anhydrous or calcined $MgSO_4$ in the manufacture of a nutritional or pharmaceutic composition for the purpose of effectively removing/mopping up adventitious water.

The use of such compounds in the manufacture of nutritional and pharmaceutical products means manufacturing can be simplified and costs reduced.

According to yet a further aspect of the present invention there is provided a method of manufacturing a nutritional or pharmaceutical composition comprising one or more components which contain water which is releasably bound wherein the manufacturing steps are conducted in the absence of special low humidity conditions and one or more anhydrous compounds are intimately mixed in the product in an amount capable of sequestering any water which may be released from the water containing components to provide a continuous desiccant effect.

The various aspect of die invention will now be described, by way of example only, with reference to the following example compositions and supporting data.

The method of preserving compositions so that they have optimum stability is illustrated by the following examples.

Carbonates and bicarbonates of group I and group II alkali metal elements and ammonia (referred to here as base components) react with acids to give carbon dioxide, and they are the basis of effervescent products when added to water. Pharmaceutically and nutritionally acceptable carbonates that can be used in effervescent compositions are carbonates and acid carbonates of ammonia, lithium, sodium, potassium, calcium and magnesium. Suitable fruit acids are illustrated by (but not limited to) citric, malic, fumaric, tartaric, ascorbic, and lactic acid. The acid component may be a partially neutralised salt of an acid having more than one acidic group. Some of the fruit acids contain water of crystallisation.

Thus, for example citric acid monohydrate contains water of crystallisation which can be driven off by heating. In tests 5.1% by weight of water is driven off on heating to 105° C. The amount of water is sufficient to cause instability in sachet preparations where the dose amount is confined in a sealed space and subject to variations of temperature.

Table 1 shows the rate of loss of water from some efflorescent salts, and other compounds when weighed quantities were dried in a temperature controlled oven at 105° C. for two hours, removed from the oven and allowed to cool in a desiccator before re-weighing.

TABLE 1

| COMPOUND | Percentage weight loss on drying at 105° C. Time in hours | | | |
|---|---|---|---|---|
| | 0 | 1 | 2 | 3 |
| Calcium Ascorbate | 0 | 4.9 | 6.5 | 7.7 |
| Calcium Lactate (Pentahydrate) | 0 | 24.1 | 24.2 | 23.7 |
| Calcium Lactate/Lactic acid adduct | 0 | 40.6 | 48.8 | 49.4 |
| Calcium Lactate (Anhydrous) | 0 | 1.5 | 2.8 | 3.6 |
| Calcium Oxide | 0 | −1.3 | −4.2 | −6.3* |
| Calcium Hydroxide | 0 | 1.8 | 2.9 | 3.2 |
| Calcium Sulphate | 0 | 19.1 | 21.3 | 21.5 |
| Magnesium Sulphate (heptahydrate) | 0 | 42.3 | 44.1 | 43.4 |
| Magnesium Sulphate (anhydrous) | 0 | −0.9 | 1.1 | −2.29* |

*A negative value indicates an increase in weight

The results show that anhydrous magnesium sulphate takes up moisture even in the drying conditions obtaining in an oven at 105° C. Under the same conditions moisture locked up as water of crystallisation in magnesium sulphate heptahydrate is removed. Similarly, calcium oxide absorbs moisture even when dried in an oven at 105° C.

Calcium lactate, and lactic acid adduct is a proprietary product made by adding calcium carbonate to an 88% solution of Lactic Acid. This gives a crystalline material that corresponds to the pentahydrate, and not to the anhydrous form.

Table 2 illustrates the loss of water from magnesium sulphate heptahydrate, and the temperature at which loss of water occurs.

TABLE 2

Loss of Water from Magnesium Heptahydrate on heating

| Temperature ° C. | No. of molecules of water lost |
|---|---|
| Ambient | 1 |
| 70–80° C. | 4 |
| 100° C. | 5 |
| 120° C. | 6 |
| 250° C. (Calcined) | 7 |

It shows the progressive effect of heating on the loss of water of crystallisation, and the efficacy of magnesium sulphate is greatest when all of the water has been removed. At a lesser degree of dehydration (when the average weight of water of crystallisation corresponds to more than one molecule of water per molecule of magnesium sulphate) the drying effect of magnesium sulphate is reduced. It is optimal when material is dried or calcined at a temperature greater than 120° C. This anhydrous $MgSO_4$ contains less than, on average, one molecule of water whereas calcined $MgSO_4$ has had substantially all of the water of crystallisation driven off.

Incorporation of dried magnesium sulphate as a magnesium source, in combination with a soluble calcium salt, provides a nutritionally acceptable material that is not hygroscopic, under normal manufacturing conditions.

EXAMPLE METHODS

A solution of calcium lactate is sprayed into the top of a drying tower in which the temperature of the air is 220–250° C. Water in the injected droplets reaches boiling point instantaneously and the latent heat of vaporisation reduces the temperature of the resulting solids. Typically, the temperature of the spray-dried solids is 40–50° C. at the base of the column, and die dwell-ime for particles in the spray dryer is 3–10 seconds. The resulting spray-dried calcium lactate contains 4% of water, i.e., it consists principally of the anhydrous salt. The powder is removed into a drum capable of being sealed and 5.5% of freshly calcined magnesium sulphate is added to the powder and thoroughly mixed. The amount of man magnesium sulphate added is in excess of the amount required to sequester water and provides a continuing desiccant effect under normal handling conditions. The amount can be calculated in accordance with the theoretical desiccant activity set out below.

Calcium lactate may also be prepared from ethyl lactate. The calculated amount of ethyl lactate is stirred into a suspension of calcium oxide in ethanol with vigorous stirring. The white solid is removed from the supernatant and dried in a fluid bed dryer. The resulting powder contains anhydrous calcium lactate and calcium hydroxide. Ethyl lactate is volatile (bp 154° C.) and is removed during drying or solvent recovery.

Theoretical Desiccant Activity

1. $MgSO_4 + 7H_2O$ 119 g of Mag Sulph Exsicc. will take up 7 moles (126 g) of water of crystallisation.

1 g of Mag Sulph Exsicc. will take up 126/119 g=1.059 g water, and provides 23/119×1000=193.3 mg of Mg.

2. $CaO + H_2O = Ca(OH)_2$ 56 g of CaO reacts with 18 g of $H_2O$ 1 g of CaO reacts with 18/56=0.3214 g water, and provides 40/56×1000=714.3 mg Ca.

3. 1 g of calcium lactate pentahydrate (CAPH) contains 25% water=250 mg 4. 1 g of anhydrous calcium lactate (CL) contains (say) 4% water=40 mg of water.

5. To mop up the water in 1 g of CL requires a) For anhydrous CL–40×1.059×1000=42.36 mg $MgSO_4$
   b) For CLPH–250/1.059×1000=264.8 mg $MgSO_4$
   c) For anhydrous CL–40×0.7143=28.57 mg CaO
   d) For CLPH–250×0.7143=178.6 mg CaO Example 1

A compound electrolyte powder containing calcium lactate (as the pentahydrate) tends to "cake" on storage at ambient temperature in the absence of a desiccant bag. One method of minimising caking is to store the composition in well-sealed containers containing a desiccant bag of a drying agent such as silica gel. In the preparation of effervescent tablets it is necessary to carry out manufacture in an environment with a low relative humidity. A free flowing powder which can be used in manufacture using normal handling conditions can be made by extracting most of the water of crystallisation and locking up the remainder by admixture with an anhydrous compound which has greater avidity for water than calcium lactate.

Calcium lactate is a preferred source of calcium in nutritional compositions and compositions which are "anhydrous" or have a low concentration of water they can be prepared by the following methods:

1. Spray-drying a saturated solution/suspension of calcium lactate pentahydrate. Drying calcium lactate pentahydrate at a temperature of 90–110° C. This temperature does not cause decomposition or chemical rearrangement, or
2. By reacting calcium oxide with ethyl lactate in a non aqueous solvent such as ethanol or n-propanol.

The "anhydrous" calcium lactate produced by one of the processes described above is immediately mixed intimately with up to 10% (and preferably 1–5%) of dried magnesium sulphate nor up to 10% (and preferably 4–8%) of calcium oxide. The amounts of magnesium sulphate and/or calcium oxide are in excess of the amount required to sequester the calculated amount of residual moisture and this will provide a cooking desiccant effect under normal handling conditions.

The resulting powder is referred to as "compound calcium lactate powder" (CCLP) in the following examples. CCLP may be used as a constituent in the formulation of other solid dose form compositions. In the following examples a powder containing magnesium sulphate (1.8%) and calcium oxide (5.8%) is used to illustrate the method. The "anhydrous" calcium lactate accounts for the remainder of the composition. The recommended daily allowance of calcium and magnesium vary from country to country and the quantitative composition of the compound powder can be adjusted to meet specific manufacturing requirements by the skilled man using the teaching of this example.

Example 2 is a formulation providing powder for preparation of an effervescent drink.

Example 2

A compound powder is prepared by mixing the following. Quantities are by weight and 5.9 g of the powder is sufficient to provide 100% of the RDA of calcium, 20% of the RDA of magnesium, and 100% of the RDA of ascorbic acid This composition is a powder to be used, when added to water, as an effervescent drink.

| Spray-dried powder as described in Example 1 | 1.1 g |
|---|---|
| Anhydrous calcium ascorbate | 0.1 g |
| Anhydrous citric acid | 3.0 g |
| Sodium bicarbonate | 1.0 g |
| Magnesium carbonate | 0.2 g |
| Precipitated calcium carbonate | 1.5 g |

Portions of 6.9 g are dispensed into laminated foil sachets and sealed in the conventional manner. The sachets are stable enough to support a shelf life claim of at least 1-year at ambient temperature. When required for use, the contents of the sachet are added to approximately 150–200 ml of water and stirred to produce a refreshing effervescent calcium-enriched drink.

Example 3

A compound mineral and multivitamin powder is prepared by mixing the following. Quantities are by weight and 7.13 g of the powder is sufficient to provide 100% of the RDA of calcium 20% of the RDA of magnesium, and 100% of the RDA of Vitamins A, B, C, D and E together with trace elements for which RDAs have not been determined. It is conventional to use a commercially available blend of vitamins.

| Vitamin blended powder | 1.0 g |
|---|---|
| Spray-dried powder as described in Example 1 | 1.5 g |
| Anhydrous calcium ascorbate | 0.1 g |
| Anhydrous citric acid | 3.0 g |
| Sodium bicarbonate | 1.0 g |
| Magnesium carbonate | 0.18 g |
| Calcium carbonate (precipitated) | 1.3 g |
| Zinc Sulphate | 0.05 g |
| Ferrous Sulphate | 0.01 g |
| Copper Sulphate | 0.002 g |
| Selenium Yeast Complex | 0.001 g |
| Manganese Sulphate | 0.001 g |
| | 7.644 g |

Portions of 7.644 g are dispensed into laminated foil sachets and heat-sealed in the conventional manner. The sachets are stable enough to support a shelf-life claim of at least 1-year at ambient temperature. When required for use, the contents of the sachet are added to approximately 150 ml of water and stored to produce a refreshing effervescent drink.

Example 4

A compound powder is prepared by mixing the following components. Quantities are given by weight. Twelve grams of the powder is sufficient to provide 100% of the RDA of calcium, 20% of the RDA of magnesium, and 100% of the RDA of ascorbic acid.

| Spray-dried powder as described in Example 1 | 10.0 g |
|---|---|
| Anhydrous Malic Acid | 8.0 g |
| Sodium benzoate | 0.175 g |
| Asesulfame | 0.15 g |
| Aspartame | 0.07 g |

To prepare a carbonated drink, 19.3 kg of this powder is dissolved in 1000 litres of potable water, filtered, sterilised by UV radiation and carbonated with up to 4 volumes of carbon dioxide. The mineralised water so produced provides 100% of the RDA of calcium and 20% of the RDA of magnesium.

Example 5

A compound powder is prepared by mixing the following components. The quantities are given by weight.

| Compound Calcium Lactate Powder as described in Example 1 | 6.4 g |
|---|---|
| Anhydrous Malic Acid | 5.0 g |
| Light Magnesium carbonate BP | 0.75 g |

When 12.15 kg of this powder is dissolved in 1000 liters of water, mineralised water is produced to which can be added fruit flavours, fruit juices, colours sweeteners and optionally, carbon dioxide to provide a mineral enriched drink. 600 ml of this drink will provide 100% of the RDA of calcium and 40% of the RDA of magnesium.

Example 6

A concentrate for preparation of a mineralised hot drink is prepared by mixing the following.

| | |
|---|---|
| Powder described in Example 1 | 28.7 g |
| Concentrated mixed fruit juice (8x) | 150 g |
| Calcium Sulphite (Anhydrous) | 0.1 g |
| Flavouring | 0.2 g |

The mixture is heated and kept at a temperature of 110° C., for 5 minutes, allowed to cool to 60° C., 20 ml quantities filled into sachets and sealed. For use, the contents of the sachet are dissolved in 150 ml of water to provide a refreshing and comforting drink containing 75% of the RDA of calcium, 100% of the RDA of Vitamin C and 20% of the RDA of magnesium.

The premix, CCLP, can be used to mineralise confectionary, Traditionally, confectionery products contain sucrose or corn syrup as a sweetening agent. Both of these substances leave a residue of sugar in the saliva which will be subject to bacterial degradation and acidification. The products of degradation may result in tooth decay (dental caries) which is particularly serious in children. It has been found that confectionery products of a type popular with young children can be fortified with minerals without loss of palatability. The powder described in Example 1 can be used to provide a re-mineralising concentration of calcium and magnesium, and is a contribution to the prevention of dental caries in young children. The methods of manufacture of confectionery will be familiar to the man skilled in art, particularly those relating to qualative and quantative aspects of flavour and sweetness. These can be modified within the teaching of the disclosure to produce mineral supplements suitable for particular therapeutic needs.

What is claimed is:

1. An ingestible composition which provides a source of digestible calcium and magnesium and, which, when added to a compound containing releasably bound water, provides a dessicating effect, said composition comprising:
   substantially anhydrous calcium lactate; calcium oxide and substantially anhydrous or calcined magnesium sulfate.

2. The composition recited in claim 1, wherein the total percent by weight of calcium lactate is greater than the combined percentage by weight of said anhydrous or calcined magnesium sulfate and said calcium oxide.

3. The composition recited in claim 1, further including a carbonate selected from the group consisting of carbonates and bicarbonates, and mixtures thereof.

4. The composition recited in claim 1, wherein said calcium oxide is present in an amount up to 10% by weight of the composition.

5. The composition recited in claim 1, wherein the anhydrous or calcined magnesium sulfate is present in an amount up to 10% by weight of the composition.

6. The composition recited in claim 1, wherein said calcium oxide forms from 4% by weight to 8% by weight of the composition.

7. The composition recited in claim 1, wherein said anhydrous or calcined magnesium sulfate forms from 1% by weight to 5% by weight of the composition.

8. The composition recited in claim 1, wherein both anhydrous magnesium sulfate and calcined magnesium sulfate are present in the composition.

9. The composition recited in claim 3, wherein said carbonate is an alkalai metal carbonate.

10. The composition recited in claim 3, wherein said bicarbonate is an alkalai metal carbonate.

11. The composition recited in claim 1, further including ammonia.

12. The composition recited in claim 3, further including an acid capable of reacting with said carbonate to liberate carbon dioxide.

13. The composition recited in claim 12, wherein said acid is a fruit acid.

14. The composition recited in claim 3, wherein said carbonates and bicarbonates are carbonates and bicarbonates of ammonia, lithium, sodium, potassium, calcium and magnesium, and combinations thereof.

15. The composition recited in claim 13, wherein said fruit acid is selected from the group consisting of citric acid, malic acid, fumaric acid, tartaric acid, ascorbic acid, lactic acid and combinations thereof.

* * * * *